United States Patent [19]

Hofer et al.

[11] 4,112,081
[45] Sep. 5, 1978

[54] O,O-DI-ALKYL-O-(1-6-PYRIDAZINON-3-YL)-(THIONO)-PHOSPHORIC ACID ESTERS AND THEIR PESTICIDAL USE

[75] Inventors: Wolfgang Hofer; Fritz Maurer; Hans-Jochem Riebel, all of Wuppertal; Ingeborg Hammann, Cologne; Wolfgang Behrenz, Overath-Steinenbrueck, all of Germany

[73] Assignee: Bayer Aktiengesellschaft, Leverkusen, Germany

[21] Appl. No.: 694,417

[22] Filed: Jun. 9, 1976

[30] Foreign Application Priority Data

Jun. 27, 1975 [DE] Fed. Rep. of Germany ....... 2528692

[51] Int. Cl.$^2$ ............................................. A01N 9/36
[52] U.S. Cl. .................................. 424/200; 544/232; 544/240
[58] Field of Search ................. 260/250 AP; 424/200

[56] References Cited

U.S. PATENT DOCUMENTS 2,759,937  8/1956  Du Brevil ..................... 260/250 AP

FOREIGN PATENT DOCUMENTS

47/20,025  12/1969  Japan.

Primary Examiner—Donald G. Daus
Assistant Examiner—Mark L. Berch
Attorney, Agent, or Firm—Burgess, Dinklage & Sprung

[57] ABSTRACT

O,O-Di-alkyl-O-(1-6-pyridazinon-3-yl)-(thiono)-phosphoric acid esters of the formula

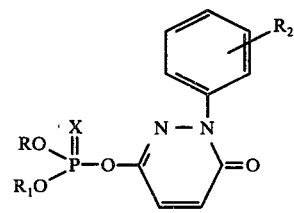

in which
R is methyl or ethyl,
$R_1$ is alkyl with 3 to 5 carbon atoms or alkoxyalkyl with 1 to 3 carbon atoms in each alkoxy and alkyl moiety,
$R_2$ is hydrogen, nitro, halogen or alkyl with 1 to 6 carbon atoms, and
X is oxygen or sulfur, which possess insecticidal and acaricidal properties.

8 Claims, No Drawings

O,O-DI-ALKYL-O-(1-6-PYRIDAZINON-3-YL)-(THIONO)-PHOSPHORIC ACID ESTERS AND THEIR PESTICIDAL USE

The present invention relates to and has for its object the provision of particular new O,O-di-alkyl-O-(1,6-pyridazinon-3-yl)-(thiono)-phosphoric acid esters which possess insecticidal or acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is already known from U.S. Pat. No. 2,759,937 that O,O-dialkyl-O-pyridazinyl-(thiono)phosphoric acid esters, for example O,O-diethyl-O-[1-phenyl-pyridazin-3-yl]-phosphoric (Compound A) and -thionophosphoric (Compound B) acid esters, possess insecticidal and acaricidal properties.

The present invention provides pyridazinyl(thiono)-phosphoric acid esters of the general formula

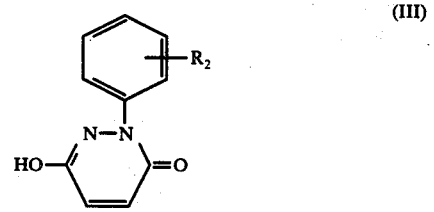

in which
R is methyl or ethyl,
$R_1$ is alkyl with 3 to 5 carbon atoms or alkoxyalkyl with 1 to 3 carbon atoms in each alkoxy and alkyl moiety,
$R_2$ is hydrogen, nitro, halogen or alkyl with 1 to 6 carbon atoms, and
X is oxygen or sulfur.

Surprisingly, the pyridazinyl(thiono)phosphoric acid esters according to the invention show a better insecticidal and acaricidal action than the corresponding previously known compounds of analogous structure and of the same type of action. The products according to the present invention thus represent a genuine enrichment of the art.

The invention also provides a process for the production of a pyridazinyl(thiono)phosphoric acid ester of the formula (I) in which a (thiono)phosphoric acid diester halide of the general formula

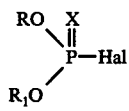

in which R, $R_1$ and X have the abovementioned meanings and Hal is halogen, preferably chlorine, is reacted with 1-phenyl-3-hydroxy-6-pyridazinone derivative of the formula (III)

in which $R_2$ has the abovementioned meaning, optionally in the presence of an acid acceptor and optionally in the presence of a solvent.

If, for example, O-ethyl-O-n-propyl-phosphoric acid diester chloride and 1-phenyl-3-hydroxy-6-oxo-pyridazlne are used as starting materials, the course of the reaction can be represented by the following formula scheme:

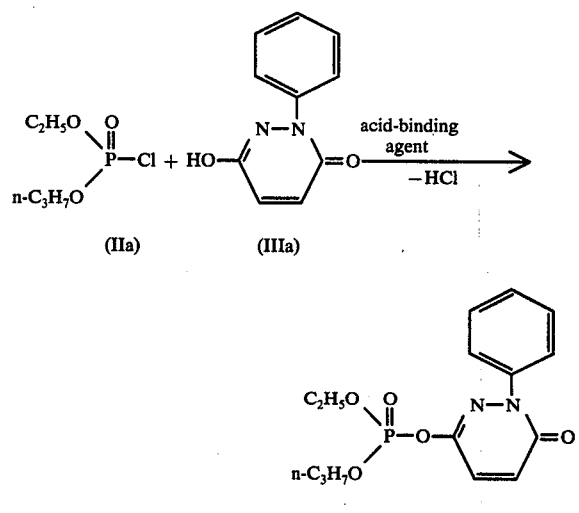

The (thiono)phosphoric acid ester halides (II) to be used as starting materials are known and can be prepared in accordance with processes known from the literature, as can the 1-phenyl-3-hydroxy-6-pyridazinone derivatives (III) [compare Du Breuil, J. Org. Chem. 26 (1961), pages 3,382–3,386].

The following may be mentioned as examples of (thiono)-phosphoric acid diester halides (II): O-methyl-O-n-propyl-, O-methyl-O-iso-propyl-, O-methyl-O-n-butyl-, O-methyl-O-iso-butyl-, O-methyl-O-sec-butyl-, O-ethyl-O-n-propyl-, O-ethyl-O-iso-propyl-, O-ethyl-O-n-butyl-, O-ethyl-O-iso-butyl-, O-ethyl-O-sec.-butyl-, O-ethyl-O-ethoxypropyl- and O-ethyl-O-ethoxyethyl-phosphoric acid diester chloride and the corresponding thiono analogues.

The following may be mentioned as examples of 1-phenyl-3-hydroxy-6-pyridazinone derivatives (III): 1-phenyl-, 1-[4-chlorophenyl]-, 1-[4-methylphenyl]-, 1-[3-chlorophenyl]-, 1-[3-methyl phenyl]-, 1-[4-ethylphenyl]-, 1-[3-ethylphenyl]- and 1-[3-nitrophenyl]-3-hydroxy-6-pyridazinone.

The reaction according to the invention is preferably carried out in the presence of a solvent (this term includes a mere diluent). Practically all inert organic solvents can be used for this purpose. They include, in particular, aliphatic, and aromatic optionally chlorinated hydrocarbons, for example benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, for example acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at 0° to 120° C, preferably at 25° to 60° C.

In general, the reaction is allowed to take place under normal pressure.

To carry out the process, the starting materials are preferably employed in equimolar amounts. An excess of one or other reactant produces no significant advantages. The reaction is in most cases carried out in one of the abovementioned solvents, at the indicated temperature. After stirring for from one to several hours, the reaction solution may be cooled and poured into an organic solvent, for example toluene. The organic phase may be worked up in the usual manner by washing, drying and distilling off the solvent.

The new compounds are obtained in the form of oils which in most cases cannot be distilled without decomposition, but may be freed from the last volatile constituents by so-called "slight distillation", that is to say by prolonged heating under reduced pressure to moderately elevated temperatures, and they may be purified in this way. They are characterized by the refractive index.

As already mentioned, the pyridazinyl(thiono)phosphoric acid esters according to the invention are distinguished by an outstanding insecticidal and acaricidal activity. They are active against plant pests, hygiene pests and pests of stored products and combine a low phytotoxicity with a good action against both sucking and biting insects and mites.

For this reason, the compounds according to the invention can be employed successfully as pesticides in plant protection and in the hygiene field and the field of protection of stored products.

To the sucking insects there belong, in the main, aphids (*Aphididae*) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (*Coccina*), for example the oleander scale (*Aspidiotus hederae*) and the soft scale (*Lecanium hesperidum*) as well as the grape mealybug (*Pseudococcus maritimus*); thrips (*Thysanoptera*), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly and moth caterpillars (*Lepidoptera*) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (*Coleoptera*), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius = Acanthoscelides obtectus*), the leather beetle (*Dermestes frischi*), the khapra beetle (*Trogoderma granarium*), the flour beetle (*Tribolium castaneum*), the northern corn billbug (*Calandra or Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Argriotes spec.*) and larvae of the cockchafer (*Melolontha melolontha*); cockroaches, such as the German cockroach (*Blattella germanica*), American cockroach (*Periplaneta americana*), Madeira cockroach (*Leucophaea or Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The *Diptera* comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes, such as the yellow fever mosquito (*Aedes aegypti*), the northern house mosquito (*Culex pipiens*) and the malaria mosquito (*Anopheles stephensi*).

With the mites (Acari) there are classed, in particular, the spider mites (Tetranychidae) such as the two-spotted spider mite (*Tetranychus urticae*) and the European red mite (*Paratetranychus pilosus = Panonychus ulmi*), gall mites, for example the black currant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against hygiene pests and pests of stored products, particularly flies and mosquitoes, the process products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal tempertures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose; emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or fungicides, nematocides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very different atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated without limitation, by the following examples:

EXAMPLE 1

Plutella test
    Solvent: 3 parts by weight of acetone
    Emulsifier: 1 by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following Table 1:

Table 1
(Plutella test)

| Active compound | Active compound concentration in % | Degree of destruction in % after 3 days |
|---|---|---|
| [Structure: O=P(OC₂H₅)₂–O–pyridazinone–phenyl] (known) (A) | 0.1<br>0.01<br>0.001 | 100<br>75<br>0 |
| [Structure: S=P(OCH₃)(OC₃H₇-n)–O–pyridazinone–phenyl] (1) | 0.1<br>0.01<br>0.001 | 100<br>100<br>100 |
| [Structure: S=P(OCH₃)(OC₃H₇-n)–O–pyridazinone–phenyl-NO₂] (6) | 0.1<br>0.01<br>0.001 | 100<br>100<br>70 |
| [Structure: S=P(OC₂H₅)(OC₃H₇-n)–O–pyridazinone–phenyl-Cl] (10) | 0.1<br>0.01<br>0.001 | 100<br>100<br>90 |
| [Structure: S=P(OC₂H₅)(OC₃H₇-n)–O–pyridazinone–phenyl-NO₂] (7) | 0.1<br>0.01<br>0.001 | 100<br>100<br>100 |

EXAMPLE 2

Laphygma test

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cotton leaves (*Gossypium hirsutum*) were sprayed with the preparation of the active compound until dew-moist and were then infested with caterpillars of the owlet moth (*Laphygma exigua*).

After the specified periods of time, the destruction in % was determined. 100% means that all caterpillars had been killed while 0% indicates that no caterpillars had been killed.

The active compounds, the concentrations of the active compounds, the evaluation times and the results can be seen from the following Table 2:

Table 2
(Laphygma test)

| Active compound | Active compound concentration in % | Degree of destruction in % after 3 days |
|---|---|---|
| [Structure: S=P(OC₂H₅)₂–O–pyridazinone–phenyl] (known) (B) | 0.1<br>0.01<br>0.001 | 100<br>100<br>0 |
| [Structure: O=P(OC₂H₅)₂–O–pyridazinone–phenyl] (known) (A) | 0.1<br>0.01<br>0.001 | 100<br>100<br>0 |
| [Structure: S=P(OCH₃)(OC₃H₇-n)–O–pyridazinone–phenyl] (1) | 0.1<br>0.01<br>0.001 | 100<br>100<br>100 |
| [Structure: S=P(OC₂H₅)(OC₃H₇-n)–O–pyridazinone–phenyl-NO₂] (7) | 0.1<br>0.01<br>0.001 | 100<br>100<br>100 |

EXAMPLE 3

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compound, the evaluation times and the results can be seen from the following Table 3:

Table 3

| (Myzus test) | | |
|---|---|---|
| Active compound | Active compound concentration in % | Degree of destruction in % after 1 day |
| [structure: O—P(OC$_2$H$_5$)$_2$, S; pyridazinone-phenyl] (known) (B) | 0.1 0.01 0.001 | 100 95 0 |
| [structure: O—P(OC$_3$H$_7$-n)(OCH$_3$), S; pyridazinone-phenyl] (1) | 0.1 0.01 0.001 | 100 100 90 |

EXAMPLE 4

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the common or two-spotted spider mite (*Tetranychus urticae*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following Table 4:

Table 4

| (Tetranychus test) | | |
|---|---|---|
| Active compound | Active compound concentration in % | Degree of destruction in % after 2 days |
| [structure: O—P(OC$_2$H$_5$)$_2$, O; pyridazinone-phenyl] (known) (A) | 0.1 | 20 |
| [structure: O—P(OC$_2$H$_5$)(OC$_3$H$_7$-n), S; pyridazinone-phenyl] (4) | 0.1 | 100 |
| [structure: O—P(OC$_2$H$_5$)(OC$_3$H$_7$-iso), S; pyridazinone-phenyl] (3) | 0.1 | 98 |

EXAMPLE 5

LD$_{100}$ test
Test insects: *Sitophilus granarius*
Solvent: Acetone 2 parts by weight of the active compound were taken up in 1,000 parts by volume of the solvent. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m$^2$ of filter paper varied with the concentration of the solution of active compound. About 25 test insects were then placed in the Petri dish and it was covered with a glass lid.

The condition of the test insects was observed 3 days after the commencement of the experiments. The destruction, in %, was determined. 100% denotes that all test insects had been killed; 0% denotes that no test insects had been killed.

The active compounds, the concentrations of the active compounds, the test insects and the results can be seen from the following Table 5:

Table 5

(LD$_{100}$ test/*Sitophilus granarius*)

| Active compound | Active compound concentration of the solution in % | Degree of destruction in % |
|---|---|---|
| (known) (B) [O-P(OC$_2$H$_5$)$_2$ with S, pyridazinone-phenyl] | 0.2<br>0.02 | 100<br>0 |
| (known) (A) [O-P(OC$_2$H$_5$)$_2$ with O, pyridazinone-phenyl] | 0.2<br>0.02 | 100<br>0 |
| (6) [S=P(OCH$_3$)(OC$_3$H$_7$-n), pyridazinone-phenyl-3-NO$_2$] | 0.2<br>0.02 | 100<br>100 |
| (7) [S=P(OC$_2$H$_5$)(OC$_3$H$_7$-n), pyridazinone-phenyl-3-NO$_2$] | 0.2<br>0.02 | 100<br>100 |
| (9) [S=P(OC$_2$H$_5$)(OC$_3$H$_7$-n), pyridazinone-phenyl-4-CH$_3$] | 0.2<br>0.02 | 100<br>100 |
| (10) [S=P(OC$_2$H$_5$)(OC$_3$H$_7$-n), pyridazinone-phenyl-4-Cl] | 0.2<br>0.02 | 100<br>100 |
| (11) [S=P(OC$_2$H$_5$)(OC$_3$H$_7$-n), pyridazinone-phenyl-Cl] | 0.2<br>0.02 | 100<br>95 |
| (1) [S=P(OC$_3$H$_7$-n)(OCH$_3$), pyridazinone-phenyl] | 0.2<br>0.02 | 100<br>100 |

The following further examples are set forth to illustrate, without limitation, the manner of producing the instant compounds according to the present invention:

EXAMPLE 6

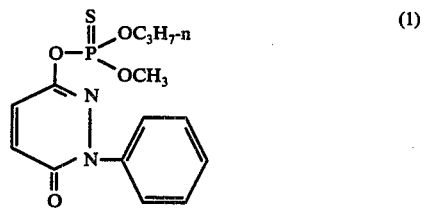

(1)

18.8 g (0.1 mole) of O-methyl-O-n-propyl-thionophosphoric acid diester chloride were added dropwise to a suspension of 18.8 g (0.1 mole) of 3-hydroxy-1-phenyl-6-pyridazinone and 14.5 g (0.105 mole) of potassium carbonate in 200 ml of acetonitrile. The reaction mixture was warmed for 3 hours to 40° C and then cooled and poured into 200 ml of toluene. The toluene solution was washed with saturated sodium bicarbonate solution and water and dried over sodium sulphate. After stripping off the solvent and subjecting the product to slight distillation, 24 g (71% of theory) of O-methyl-O-n-propyl-O-[1-phenyl-6-pyridazinon-3-yl]-thiono-phosphoric acid ester were obtained in the form of a yellow oil of refractive index $n_D^{21}$: 1.5696.

The following compounds of the formula (I) can be prepared analogously:

Table 6

| Compound No. | X | R | R$_1$ | R$_2$ | Yield (% of theory) | Physical data (refractive index) |
|---|---|---|---|---|---|---|
| 2 | S | C$_2$H$_5$ | CH$_2$—CH(CH$_3$)$_2$ | H | 77 | $n_D^{18}$: 1.5561 |
| 3 | S | C$_2$H$_5$ | C$_3$H$_7$-iso | H | 73 | $n_D^{18}$: 1.5630 |
| 4 | S | C$_2$H$_5$ | C$_3$H$_7$-n | H | 68 | $n_D^{23}$: 1.5521 |
| 5 | S | C$_2$H$_5$ | CH$_2$—CH$_2$—OC$_2$H$_5$ | H | 68 | $n_D^{24}$: 1.5408 |
| 6 | S | CH$_3$ | C$_3$H$_7$-n | 3-NO$_2$ | 63 | $n_D^{23}$: 1.5813 |
| 7 | S | C$_2$H$_5$ | C$_3$H$_7$-n | 3-NO$_2$ | 67 | $n_D^{23}$: 1.5675 |
| 8 | S | CH$_3$ | C$_3$H$_7$-n | 4-CH$_3$ | 88 | $n_D^{22}$: 1.5484 |
| 9 | S | C$_2$H$_5$ | C$_3$H$_7$-n | 4-CH$_3$ | 92 | $n_D^{23}$: 1.5478 |

Table 6-continued

| Compound No. | X | R | R₁ | R₂ | Yield (% of theory) | Physical data (refractive index) |
|---|---|---|---|---|---|---|
| 10 | S | C₂H₅ | C₃H₇-n | 4-Cl | 72 | $n_D^{21}$: 1.5738 |
| 11 | S | C₂H₅ | C₃H₇-n | 3-Cl | 77 | $n_D^{21}$: 1.5689 |

Other compounds which can be similarly prepared include:

Table 7

| Compound No. | X | R | R₁ | R₂ |
|---|---|---|---|---|
| 12 | O | C₂H₅ | C₃H₇-n | H |
| 13 | O | CH₃ | C₃H₆—O—C₃H₇ | 2-Br |
| 14 | S | CH₃ | CH₂—O—CH₃ | 4-C₄H₉ |
| 15 | S | CH₃ | CH₃ | 4-F | and the like.

It will be appreciated that the instant specification and examples are set forth by way of illustration and not limitation, and that various modifications and changes may be made without departing from the spirit and scope of the present invention.

What is claimed is:

1. An O,O-dialkyl-O-(1-phenyl-6-pyridazinon-3-yl)-(thiono)-phosphoric acid ester of the formula

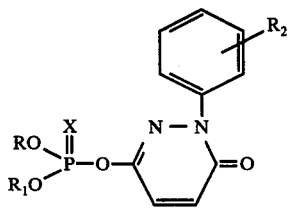

(I)

in which
R is methyl or ethyl,
R₁ is alkyl with 3 or 4 carbon atoms, methoxymethyl or ethoxyethyl, and
R₂ is hydrogen, nitro, chlorine, methyl or ethyl.

2. An insecticidal or acaricidal composition containing as active ingredient an insecticidally or acaricidally effective amount of a compound according to claim 1 in admixture with a conventional inert pesticide diluent.

3. The compound according to claim 1, wherein such compound is O-methyl-O-n-propyl-O-(1-phenyl-6-pyridazinon-3-yl)-thiono-phosphoric acid ester of the formula

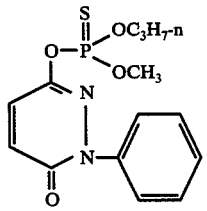

4. The compound according to claim 1 wherein such compound is O-ethyl-O-iso-propyl-O-(1-phenyl-6-pyridazinon-3-yl)-thiono-phosphoric acid ester of the formula

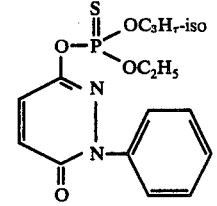

5. The compound according to claim 1 wherein such compound is O-methyl-O-n-propyl-O-[1-(3-nitrophenyl)-6-pyridazinon-3-yl]-thiono-phosphoric acid ester of the formula

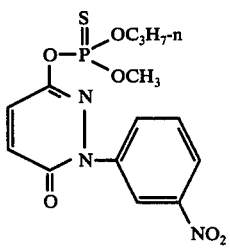

6. The compound according to claim 1 wherein such compound is O-ethyl-O-n-propyl-O-[1-(3-nitrophenyl)-6-pyridazinon-3-yl]-thiono-phosphoric acid ester of the formula

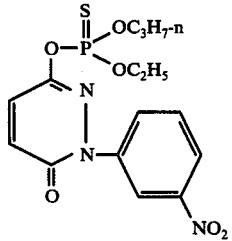

7. The compound according to claim 1 wherein such compound is O-ethyl-O-n-propyl-O-[1-(3-chlorophenyl)-6-pyridazinon-3-yl]-thiono-phosphoric acid ester of the formula

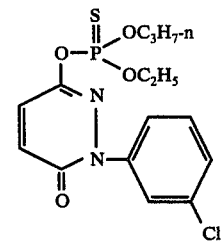

8. The method of combating insect or acarid pests which comprises applying to the pests or a habitat thereof an insecticidally or acaricidally effective amount of
O-methyl-O-n-propyl-O-(1-phenyl-6-pyridazinon-3-yl)-thiono-phosphoric acid ester,
O-ethyl-O-iso-propyl-O-(1-phenyl-6-pyridazinon-3-yl)-thiono-phosphoric acid ester,
O-methyl-O-n-propyl-O-[1-(3-nitrophenyl)-6-pyridazinon-3-yl]-thiono-phosphoric acid ester,
O-ethyl-O-n-propyl-O-[1-(3-nitrophenyl)-6-pyridazinon-3-yl]-thiono-phosphoric acid ester, or
O-ethyl-O-n-propyl-O-[1-(3-chlorophenyl)-6-pyridazinon-3-yl]-thiono-phosphoric acid ester.

* * * * *